United States Patent [19]

Barney et al.

[11] Patent Number: 4,906,573

[45] Date of Patent: Mar. 6, 1990

[54] CULTURE MEDIUM FOR DETECTION OF BEER SPOILAGE MICROORGANISMS

[75] Inventors: Michael C. Barney, Wauwatosa; Edward J. Kot, Delafield; Etzer Chicoye, Milwaukee, all of Wis.

[73] Assignee: Miller Brewing Company, Milwaukee, Wis.

[21] Appl. No.: 78,537

[22] Filed: Jul. 28, 1987

[51] Int. Cl.$^4$ .......................... C12N 1/00; C12N 1/38; C12N 1/20; C12Q 1/04
[52] U.S. Cl. ...................... 435/243; 426/16; 435/29; 435/34; 435/244; 435/253.6; 435/255; 435/256
[58] Field of Search ................... 435/29, 34, 243, 244, 435/253, 255, 256; 426/16, 330.4

[56] References Cited

U.S. PATENT DOCUMENTS 3,878,650  4/1975  Lee ................................ 435/253 X

OTHER PUBLICATIONS

Kozulis, J. A. and Page, H. E., Amer. Soc. Brew. Chem., Proc., 26:52–58, (1968).
Saha, R. B., Sondag, R. J. and Middlekauff, J. E., Amer. Soc. Brew. Chem., Proc., 32(1):90–10, (1974).
Lee, S. Y., Jangaard, N. O., Coors, J. H., Hsu, W. P., Fuchs, C. M. and Brenner, N. W., Amer. Soc. Brew. Chem., Proc., 33(1):18–25, (1975).
deMan, J. C., Rogosa, M. & Sharpe, M. E., J. Appl. Bacteriol., 23:130, (1960).

Primary Examiner—David M. Naff
Attorney, Agent, or Firm—Quarles & Brady

[57] ABSTRACT

Beer spoilage microorganisms are detected with a culture medium that is advantageous for detecting *Lactobacillus spp., Pediococcus spp.* and wild yeast, and which allows detection to be carried out in four days. The medium contains tomato juice, peptones, cysteine hydrochloride, sorbitan nonooleate, mono and disaccharides, yeast extract, beef extract, potassium acetate, malic acid, mono and dibasic potassium phosphate, magnesium sulfate, maganese sulfate, sodium chloride, ferrous sulfate, beer, water and agar.

1 Claim, No Drawings

CULTURE MEDIUM FOR DETECTION OF BEER SPOILAGE MICROORGANISMS

FIELD OF THE INVENTION

The present invention relates to a culture medium and method for the growth of microorganisms. More particularly, it relates to a culture medium and method for the selective detection of common beer spoilage microorganisms.

BACKGROUND OF THE INVENTION

Beer can be spoiled by the growth of a range of microorganisms, most commonly by Lactobacillus spp., Pediococcus spp. and wild yeast. Brewers as part of their quality control programs routinely plate beer samples upon a culture medium so as to detect any of the beer spoilage microorganisms which may be present. A typical plating procedure employs a culture medium, such as Universal Beer Agar (UBA), that can detect a wide range of beer spoilage microorganisms. Normally, incubation takes about seven days. However, even after seven days there is not adequate growth of some of the microorganisms to allow visual detection. This is especially true of the microorganisms Pediococcus spp.

In the past, there have been various attempts to develop a better universal medium that would reduce the length of incubation, but those attempts have been uniformly unsuccessful.

It would obviously be desirable to have a culture medium which makes possible a faster and more reliable method of detecting common beer spoilage microorganisms.

BRIEF SUMMARY OF THE INVENTION

It is an objective of the present invention to disclose a new improved culture medium which can be used to detect beer spoilage microorganisms.

It is also an object of the present invention to disclose a faster and more reliable method of detecting beer spoilage microorganisms which employs the culture medium of the present invention.

The culture medium of the present invention, referred to as Barney-Miller Brewery (BMB) medium, is a mixture of the following: tomato juice, known to enhance the growth of Lactobacillus spp.; peptones, a source of amino acids (nitrogen); cysteine hydrochloride, an amino acid that stimulates some *Lactobacillus spp.*; Tween 80, sorbitan monooleate, a surfactant which enables microorganisms to more effectively contact and absorb nutrients; mono and disaccharides, which serve as carbohydrate sources; yeast extract, a source of B-complex vitamins; beef extract, another source of amino acids; potassium acetate, which inhibits some non-spoiler microorganisms and serves to buffer the medium; malic acid, a carbon source for lactic acid bacteria; mono and dibasic potassium phosphate to supply phosphorous and to buffer the medium; magnesium sulfate, manganese sulfate, sodium chloride, and ferrous sulfate to supply necessary minerals, beer to supply hop acids to inhibit non-spoilers; water and agar to act as a non-nutrient solidifying agent when a solid medium is desired.

In the method of the present invention beer samples are plated onto BMB culture medium and incubated in a $CO_2$, anaerobic environment at 25°–30° C. for four to five days. The plates are then examined for colonies of beer spoilage microorganisms. The results obtained within four days are statistically equivalent to the results obtained in the seven day prior art procedure using UBA. Therefore, the method of the present invention can be substituted without disadvantage for the seven day procedure for the detection of common beer spoilage microorganisms.

The culture medium of the present invention, BMB, is superior to all known culture media used for detecting the presence of common beer spoilage microorganisms. It is particularly advantageous for detecting Pediococcus spp. because visible colonies of such microorganisms appear within four days. It also is better than the commonly employed UBA for detecting the presence of wild yeast.

DESCRIPTION OF THE PREFERRED EMBODIMENT

In the preferred embodiment of the invention beer samples are plated on a solid culture medium which has a pH of about 5.5 to about 5.7 and which is comprised of tomato juice, peptones, cysteine hydrochloride, sorbitan monooleate, yeast extract, beef extract, potassium acetate, mono and disaccharides, mono and dibasic potassium phosphate, magnesium sulfate, manganese sulfate, sodium chloride, ferrous sulfate, malic acid, beer, water and agar. The medium is sterilized by autoclaving at 121° C., 15 psig steam for 15 minutes and is typically dispensed in 25 ml aliquots into 100 mm sterile petri plates. The plates are then incubated in a $CO_2$, anaerobic environment at 25°–30° C. for four days at which time the plates are examined to detect colonies of beer spoilage microorganisms.

EXPERIMENTAL

To demonstrate the superiority of the culture medium of the present invention, it was compared to Universal Beer Agar (UBA) and the following five other commonly used brewery culture media for detection of beer spoilage organisms. The other culture media employed were Raka Ray #3; Nachweis Medium für Bierschädlichen Bakterian (NBB); Lee's Multidifferential Agar (LMDA); Hsu's Lactobacillus-Pediococcus medium (HLP); and deMan, Rogosa and Sharpe medium (MRS). In the comparison, samples of beer known to contain nine typical brewery microorganisms were plated under identical conditions on the media. The comparison included quantitative (recovery efficiencies) and qualitative (colony size) analyses.

The following microorganisms were used in this study:
Pediococcus sp. 103G - a known beer spoiler
Pediococcus sp. P2 - a known keg beer spoiler
Pediococcus sp. 177A - a known beer spoiler
Pediococcus damnosus - ATCC #29358
Lactobacillus buchneri - ATCC #11307
Lactobacillus brevis - ATCC #8291
Lactobacillus sp. FL - a known keg beer spoiler
Lactobacillus sp. PEL - a known beer spoiler
Saccharomyces sp. wild yeast, known beer spoiler
All the organisms were precultured in Universal Beer Broth (UBB=UBA prepared without agar) at 28° C. in a $CO_2$, anaerobic environment incubator for 7 days prior to the evaluation.

The media that were evaluated and their formulations were the following:

1. Culture medium of the present invention, Barney-Miller Brewery (BMB) medium - 7.3 g tomato juice, 15.0 g maltose, 13.7 g dextrose, 5.0 g Polypeptone ™ peptones, 3.7 g yeast extract, 3.0 g potassium acetate, 2.0 g beef extract, 0.5 g malic acid, 0.5 g Tween 80 (sorbitan mono-oleate), 0.2 g monopotassium phosphate, 0.2 g dipotassium phosphate, 0.2 g cysteine hydrochloride, 0.07 g magnesium sulfate, 0.004 g manganese sulfate, 0.004 g ferrous sulfate, 0.004 g sodium chloride, 15.0 g agar, 250 ml beer and 750 ml distilled water (pH 5.5–5.7).

2. Universal Beer Agar (UBA) (ref. 1)—Difco #0856-01-4-6.1 g yeast extract, 15.0 g peptonized milk, 12.2 g tomato juice solids, 16.1 g dextrose, 0.31 g dipotassium phosphate, 0.31 g monopotassium phosphate, 0.12 g magnesium sulfate, 0.006 g sodium chloride, 0.006 g ferrous sulfate, 0.006 g manganese sulfate, 12.0 g agar, 250 ml beer and 750 ml distilled water (pH 6.3).

3. Raka Ray #3 (RR3) medium (ref. 2)—20.0 g trypticase, 5.0 g yeast extract, 1.0 g liver concentrate, 10.0 g maltose, 10.0 g fructose, 2.0 g diammonium citrate, 10.0 ml Tween 80 (sorbitan mono-oleate), 2.0 g dipotassium phosphate, 2.0 g betaine hydrochloride, 2.5 g potassium aspartate, 2.5 g potassium glutamate, 0.5 g n-acetyl glucosamine, 2.0 g magnesium sulfate, 0.5 g manganese sulfate, 20.0 g agar and 1000 ml distilled water (pH 5.4).

4. Nachweis-medium für Bierschädlichen Bakterien (NBB) (ref. 3)—5.0 g Polypetone ™ peptones, 5.0 g yeast extract, 2.0 g beef extract, 15.0 g dextrose, 15.0 g maltose, 2.0 g dipotassium phosphate, 2.0 g sodium acetate, 0.5 g malic acid, 0.5 g Tween 80 (sorbitan mono-oleate), 0.2 g cysteine hydrochloride, 10.0 g agar 3.0 g gelatin and 1000 ml distilled water (pH 5.2).

Lee's Multidifferential Agar (LMDA) (ref. 4) 20.0 g tomato juice solids, 20.0 g peptonized milk, 10.0 g yeast extract, 10.0 g glucose, 2.0 g calcium pantothenate, 1.1 g citric acid, 5.0 g calcium carbonate, 0.5 g dipotassium phosphate, 0.5 g monopotassium phosphate, 0.2 g magnesium sulfate, 0.01 g manganese sulfate, 0.01 g ferrous sulfate, 0.01 g sodium chloride, 0.5 g Tween 80 (sorbitan monooleate), 0.022 g brom cresol green, 15.0 g agar with volume adjusted to 1000 ml with distilled water (pH 5.5).

6. Hsu's *Lactobacillus Pediococcus* (HLP) medium—formula not available—prepared by rehydrating 70.0 g of commercial product (J. E. Siebel Son's Company Inc., Chicago, Ill.) in 1000 ml distilled water and adding agar (pH 5.7).

7. deMan, Rogosa and Sharpe (MRS) medium (ref. 5)—Difco #0881-01-3 - 10.0 g proteose peptone #3, 10.0 g beef extract, 5.0 g yeast extract, 20.0 g dextrose, 1.0 g sorbitan mono-oleate complex (Tween 80), 2.0 g ammonium citrate, 5.0 g sodium acetate, 0.1 g magnesium sulfate, 0.05 g manganese sulfate, 2.0 g disodium phosphate, 15.0 g agar with 1000 ml distilled water (pH 6.5).

The formulations for the media listed above are presented in Table I for comparison.

The precultures of the test microorganisms were serially diluted in Universal Beer Broth and were seeded into bottles of pasteurized commercial beer. 50 ml aliquots (i.e., each bottle was split into seven aliquots so that all filtered plated samples were taken from the same stock) of seeded beer were filtered through sterile Millipore 47 mm, 0.45μ, black-grid membrane filters. The filters were then incubated (grid side up) on plates of the seven different media. All of the media were prepared according to the reference instructions. The plates were incubated in a $CO_2$, anaerobic environment at 28° C. for seven days with counts and observations of colony sizes being made daily starting after 2 days of incubation.

The culture medium of the present invention, Barney-Miller Brewery (BMB) medium, was superior to all other media tested for culturing Pediococcus spp. in that it produced the largest colonies and gave consistently high recoveries. It also performed better than UBA for all of the Lactobacillus spp. tested although it was not necessarily the best medium of the seven tested for some individual organisms. Overall, it was the best medium by far, because it produced colonies that could be easily counted in four days and consistently gave high recoveries.

Table II presents plate count and colony size data for the four Pediococcus spp. that were tested. In all four cases detectable colonies were recovered on the BMB medium within four days. Although NBB on two occasions produced higher recoveries, the colony sizes were significantly smaller than those on BMB. BMB performed as well or better than all other media with each of the organisms tested. BMB had a significantly better recovery of Pediococcus spp. than that of UBA and in all cases could produce larger colonies than UBA. For the cocci tested the order of preference (considering recovery and colony size) was BMB, UBA, NBB, LMDA, MRS, RR3, and HLP.

Table III presents plate count and colony size data for the four Lactobacillus spp. and the one wild yeast that were investigated. Some of the media produced larger colonies of the Lactobacillus spp. than BMB, however, the recovery rate was inferior to BMB. Only MRS had consistent recoveries equivalent to BMB with slightly larger colonies in two cases. However, MRS did much more poorly in recovering Pediococcus spp. In addition, BMB produced larger colonies than UBA, the commonly preferred culture medium, for all four Lactobacillus spp. tested. The recovery efficiencies of UBA and BMB were equivalent for three of the four organisms, but with Lactobacillus spp. PEL, BMB recovered significantly more bacteria than UBA. (None of the seven media tested proved superior for the isolation of the Lactobacillus spp. evaluated.) However, the culture medium of the present invention, Barney-Miller Brewery (BMB) medium, gave consistently good detection because it produced easily discernible colonies and high recoveries. The wild yeast used in this study grew well on all of the media with the exception of HLP.

TABLE I

Components of Media for Detecting Beer Spoilage Microorganisms
Media* and Concentration
(quantity/liter)

| Component | BMB | UBA | RR3 | NBB | LMDA | MRS |
|---|---|---|---|---|---|---|
| Proteose Peptone | — | — | — | — | — | 10.0 g |
| Polypeptone ™ Peptone | 5.0 g | — | — | 5.0 g | — | — |
| Trypticase | — | — | 20.0 g | — | — | — |
| Peptonized Milk | — | 15.0 g | — | — | 20.0 g | — |
| Yeast Extract | 3.7 g | 6.1 g | 5.0 g | 5.0 g | 10.0 g | 5.0 g |

TABLE I-continued

Components of Media for Detecting Beer Spoilage Microorganisms
Media* and Concentration
(quantity/liter)

| Component | BMB | UBA | RR3 | NBB | LMDA | MRS |
|---|---|---|---|---|---|---|
| Beef Extract | 2.0 g | — | — | 2.0 g | — | 10.0 g |
| Liver Concentrate | — | — | 1.0 g | — | — | — |
| Tomato Juice Solids | 7.3 g | 12.2 g | — | — | 20.0 g | — |
| Maltose | 15.0 g | — | 10.0 g | 15.0 g | — | — |
| Dextrose | 13.7 g | 16.1 g | — | 15.0 g | 10.0 g | 20.0 g |
| Fructose | — | — | 10.0 g | — | — | — |
| Sodium Acetate | — | — | — | 6.0 g | — | 5.0 g |
| Potassium Acetate | 3.0 g | — | — | — | — | — |
| Diammonium Citrate | — | — | 2.0 g | — | — | 2.0 g |
| Citric Acid | — | — | — | — | 1.1 g | — |
| Tween 80 | 0.5 g | — | 10.0 ml | 0.5 g | 0.5 g | 1.0 g |
| Malic Acid | 0.5 g | — | — | 0.5 g | — | — |
| $KH_2PO_4$ | 0.2 g | 0.31 g | — | — | 0.5 g | — |
| $K_2HPO_4$ | 0.2 g | 0.31 g | 2.0 g | 2.0 g | 0.5 g | — |
| $Na_2HPO_4$ | — | — | — | — | — | 2.0 g |
| Calcium Carbonate | — | — | — | — | 5.0 g | — |
| Cysteine HCL | 0.2 g | — | — | 0.2 g | — | — |
| Betaine HCL | — | — | 2.0 g | — | — | — |
| Potassium aspartate | — | — | 2.5 g | — | — | — |
| Potassium glutamate | — | — | 2.5 g | — | — | — |
| N—acetyl glucosamine | — | — | 0.5 g | — | — | — |
| Calcium pantothenate | — | — | — | — | 2.0 g | — |
| $MgSO_4 \cdot 7H_2O$ | 0.07 g | 0.12 g | 2.0 g | — | 0.2 g | 0.1 g |
| $MnSO_4 \cdot H_2O$ | 0.004 g | 0.006 g | 0.5 g | — | 0.01 g | 0.05 g |
| $FeSO_4$ | 0.004 g | 0.006 g | — | — | 0.01 g | — |
| NaCl | 0.004 g | 0.006 g | — | — | 0.01 g | — |
| Brom cresol green | — | — | — | — | 0.022 g | — |
| Agar | 15.0 g | 12.0 g | 20.0 g | 10.0 g | 15.0 g | 15.0 g |
| Gelatin | — | — | — | 3.0 g | — | — |
| Beer | 250 ml | 250 ml | — | — | — | — |
| Water | 750 ml | 750 ml | 1000 ml | 1000 ml | 1000 ml | 1000 ml |
| pH** | 5.7 | 6.3 | 5.4 | 5.2 | 5.5 | 6.5 |

*The formula for HLP was not available (i.e., proprietary).
**The pH values are those cited in the literature. The media were prepared and the pH adjusted by the addition of HCl or NaOH as described in the literature.

TABLE II

Colony Counts and Sizes of Four Cocci Bacteria Cultured on Seven Brewing Media

| | Colony Count/Colony Size (ave. diameter) | | | |
|---|---|---|---|---|
| Medium | Pediococcus sp. 103G | Pediococcus sp. P2 | Pediococcus sp. 177A | Pediococcus damnosus |
| BMB | 98/0.7 mm | 89/0.4 mm | 67/1.0 mm | 60/0.6 mm |
| UBA | 104/0.5 mm | 89/0.3 mm | 52/0.6 mm | 15/0.3 mm |
| RR3 | 109/0.6 mm | 79/0.3 mm | 60/0.6 mm | 0 |
| NBB | 97/0.4 mm | 120/0.2 mm | 102/0.7 mm | 2/0.2 mm |
| LMDA | 68/0.3 mm | 49/0.2 mm | 64/0.5 mm | 11/0.2 mm |
| HLP | 44/0.3 mm | 57/0.2 mm | 7/0.8 mm | 10/0.2 mm |
| MRS | N.D.* | 51/0.2 mm | 50/0.2 mm | 3/0.2 mm |
| Days of Incubation | 5 days** | 4 days | 5 days | 5 days |

*N.D. = not determined.
**Plates were checked daily but the length of incubation used for comparison was chosen based on a time that would allow detection on all of the media tested.

TABLE III

Colony Counts and Sizes of Four Lactobacilli and One Wild Yeast Cultured on Seven Brewery Media

| | Colony Count/Colony Size (ave. diameter) | | | | |
|---|---|---|---|---|---|
| Medium | Lactobacillus buchneri | Lactobacillus brevus | Lactobacillus sp. FL | Lactobacillus sp. PEL | Saccharomyces sp. Wild Yeast |
| BMB | 60/1.2 mm | 54/1.0 mm | 32/2.0 mm | 85/0.2 mm | 23/1.5 mm |
| UBA | 67/0.8 mm | 48/0.5 mm | 46/1.0 mm | 52/0.1 mm | 22/1.5 mm |
| RR3 | 52/2.5 mm | 37/0.5 mm | 3/4.0 mm | 94/0.2 mm | 26/2.0 mm |
| NBB | 79/0.6 mm | 45/0.6 mm | 24/1.0 mm | 64/0.2 mm | 20/3.0 mm |
| LMDA | 60/1.0 mm | 45/0.7 mm | 23/1.5 mm | 36/0.1 mm | 15/2.0 mm |
| HLP | 80/1.4 mm | 44/1.1 mm | 28/1.3 mm | 3/0.1 mm | 0 |
| MRS | 67/1.5 mm | 48/1.5 mm | 36/2.0 mm | 58/0.2 mm | 26/2.5 mm |
| Days of Incu- | | | | | |

TABLE III-continued

Colony Counts and Sizes of Four *Lactobacilli* and
One Wild Yeast Cultured on Seven Brewery Media

| Medium | Colony Count/Colony Size (ave. diameter) | | | | |
|---|---|---|---|---|---|
| | *Lactobacillus buchneri* | *Lactobacillus brevus* | *Lactobacillus* sp. FL | *Lactobacillus* sp. PEL | *Saccharomyces* sp. Wild Yeast |
| bation | 5 days* | 4 days | 4 days | 4 days | 2 days |

*Plates were checked daily but the length of incubation used for comparison was chosen based on a time that would allow detection on all of the media tested.

Conclusions

Overall Barney-Miller Brewery (BMB) medium was the best medium tested for detecting a wide range of beer spoilage microorganisms in beer. It had a distinct advantage over other commonly used media because it supported faster growth and it gave higher levels of recovery especially compared to the recovery of Pediococcus spp. on UBA.

The ingredients used in Barney-Miller Brewery medium are commercially available from a number of sources. The preferred peptone mixture for use in the culture medium of the present invention is Polypeptone ™ peptone, which is sold by Becton Dickinson & Co. of Cockeysville, Md. It is a water-soluble mixture of proteoses and amino acids produced by the hydrolysis of natural proteins (milk and animal proteins).

All of the ingredients employed in the culture medium of the present invention have been used in other formations of culture media, known in the art, including the peptones. In addition, the preferred pH of 5.5 to 5.7 is intermediate in the range of pH values used for culture media for detecting beer spoilage microorganisms. Therefore, it appears that it is the unique combination of ingredients and the pH of the culture medium of the present invention that contribute to its unexpected superiority over UBA and other prior art culture media.

Although for purpose of illustration a culture medium having a specific and precise formula has been described. It will be appreciated by those skilled in the art that equivalent ingredients can be substituted for those used and that the concentration of ingredients can be varied. The following is a more generic formula:

| | (w/v) |
|---|---|
| tomato juice | 0.70% |
| polypeptone | 0.50% |
| yeast extract | 0.37% |
| beef extract | 0.20% |
| maltose | 1.50% |
| dextrose | 1.37% |
| potassium acetate | 0.30% |
| sorbitan mono-oleate | 0.05% |
| monopotassium phosphate | 0.02% |
| dipotassium phosphate | 0.02% |
| cysteine hydrochloride | 0.02% |
| malic acid | 0.05% |
| magnesium sulfate | 0.007% |
| manganese sulfate | 0.0004% |

-continued

| | (w/v) |
|---|---|
| sodium chloride | 0.0004% |
| ferrous sulfate | 0.0004% |
| agar | 1.50% |
| beer | 25.00% |
| water | 68.38% |

It will be readily apparent to those skilled in the art that a number of other changes and modifications can be made without departing from the spirit and scope of the invention. Therefore, the scope of the invention is not to be limited except by the claims.

References

1. Kozulis, J. A. and Page, H. E., Amer. Soc. Brew. Chem., Proc. 26:52-58 (1968).
2. Saha, R. B., Sondag, R. J. and Middlekauf, J. E., Amer. Soc. Brew. Chem., Proc. 32(1):90-10 (1974).
3. Back, W., Brauwelt 43:1562-69 (1980).
4. Lee, S. Y., Jangard, N. O., Coors, J. H., Hsu, W. F., Fuchs, C. M. and Brenner, M. W., Amer. Soc. Brew. Chem., Proc. 33(1):18-25 (1975).
5. deMan, J. C. Rogosa, M. and Sharpe, M. E., J. Appl. Bacteriol. 23:130 (1960).

We claim:

1. A culture medium for growing beer spoilage microorganisms that may be present in beer, said medium containing the following ingredients in about the concentrations given:

| | (w/v) |
|---|---|
| tomato juice | 0.70% |
| polypeptone | 0.50% |
| yeast extract | 0.37% |
| beef extract | 0.20% |
| maltose | 1.50% |
| dextrose | 1.37% |
| potassium acetate | 0.30% |
| sorbitan mono-oleate | 0.05% |
| monopotassium phosphate | 0.02% |
| dipotassium phosphate | 0.02% |
| cysteine hydrochloride | 0.02% |
| malic acid | 0.05% |
| magnesium sulfate | 0.007% |
| manganese sulfate | 0.0004% |
| sodium chloride | 0.0004% |
| ferrous sulfate | 0.0004% |
| agar | 1.50% |
| beer | 25.00% |
| water | 68.38% |

* * * * *